United States Patent
Mestroni et al.

(12)

(10) Patent No.: US 6,221,905 B1
(45) Date of Patent: Apr. 24, 2001

(54) SALTS OF ANIONIC COMPLEXES OF RU (III), AS ANTIMETASTATIC AND ANTINEOPLASTIC AGENTS

(75) Inventors: Giovanni Mestroni; Enzo Alessio; Gianni Sava, all of Trieste (IT)

(73) Assignee: Sigea S.r.l., Trieste (IT)

( * ) Notice: Subject to any disclaimer, the term of this patent is extended or adjusted under 35 U.S.C. 154(b) by 0 days.

(21) Appl. No.: 09/214,254

(22) PCT Filed: Jun. 30, 1997

(86) PCT No.: PCT/EP97/03401

§ 371 Date: Dec. 30, 1998

§ 102(e) Date: Dec. 30, 1998

(87) PCT Pub. No.: WO98/00431

PCT Pub. Date: Jan. 8, 1998

(30) Foreign Application Priority Data

Jul. 2, 1996 (IT) .............................................. MI96A1359

(51) Int. Cl.[7] .............................. A61K 31/28; C07F 15/00
(52) U.S. Cl. ................................................... 514/492; 546/6
(58) Field of Search ................................. 514/492; 546/6

(56) References Cited

PUBLICATIONS

Alessio et al., Inorg. Chim Acta., 203 pp. 205–217, 1993.*
Sava et al. Chem. Biol. Interactions, 1995.*
Geremia et al., Inoorg. Chim Acta 253 pp. 87–90, 1996.*
Art Submitted in PCT is Reviewed WO98/00431.*
Canadian Journal of Chemistry, vol. 67, No. 3, Mar. 1989, Toronto, Press, (Canada), P.K.L. Chan et al.
Chemical Abstracts, vol. 110, 1989, (Columbus, Ohio, US), U.C. Sarma et al.
Chemical Abstracts, vol. 112, 1990, (Columbus, Ohio, US), G. Mestroni.
Journal of the Chemical Society, Dalton Transactions, 1973, I.P. Evans et al.
Chemical Abstracts, vol. 86, 1977, (Columbus, Ohio, US), T. Bora et al.

* cited by examiner

Primary Examiner—Mukund J. Shah
Assistant Examiner—Pavanaram K Sripada
(74) Attorney, Agent, or Firm—Hedman, Gibson & Costigan, P.C.

(57) ABSTRACT

A salt of an anionic complex of Ru(III) with an ammonium cation fof formula (I),

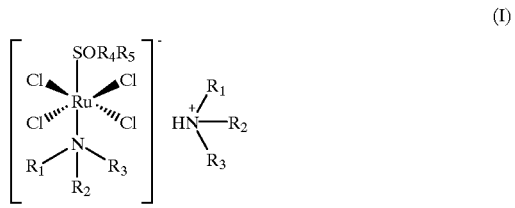

(I)

where $R_1$, $R_2$ and $R_3$, equal or different from each other, are selected from the group consisting of H, $C_1$–$C_6$ alkyl, linear or branched, saturated or unsaturated, $C_3$–$C_7$ cycloalkyl, phenyl and aryl; or $NR_1R_2R_3$ is a 5–7-membered nitrogen-containing heterocycle, saturated or unsaturated, optionally containing one or more O, S and/or N atoms, said nitrogen atom being optionally substituted with a $C_1$–$C_4$ alkyl, aryl or benzyl residue; said nitrogen-containing heterocycle being optionally condensed with a benzo group and/or substituted with $C_1$–$C_4$ alkyl, $C_1$–$C_4$ alkoxyl, $C_1$–$C_4$ alkylthio, aryl or benzyl groups; where $R_4$ and $R_5$, equal or different from each other, are selected from the group consisting of H, $C_1$–$C_6$ alkyl, $C_3$–$C_7$ cycloalkyl, phenyl and aryl or $R_4$ and $R_5$ form, together with the S atom, a 4–7-membered heterocycle. Furthermore the process for the preparation of said salts, the pharmaceutically compositions containing the same and their use as antimetastatic and antineoplastic agents are described.

23 Claims, 3 Drawing Sheets

(3 of 3 Drawing Sheet(s) Filed in Color)

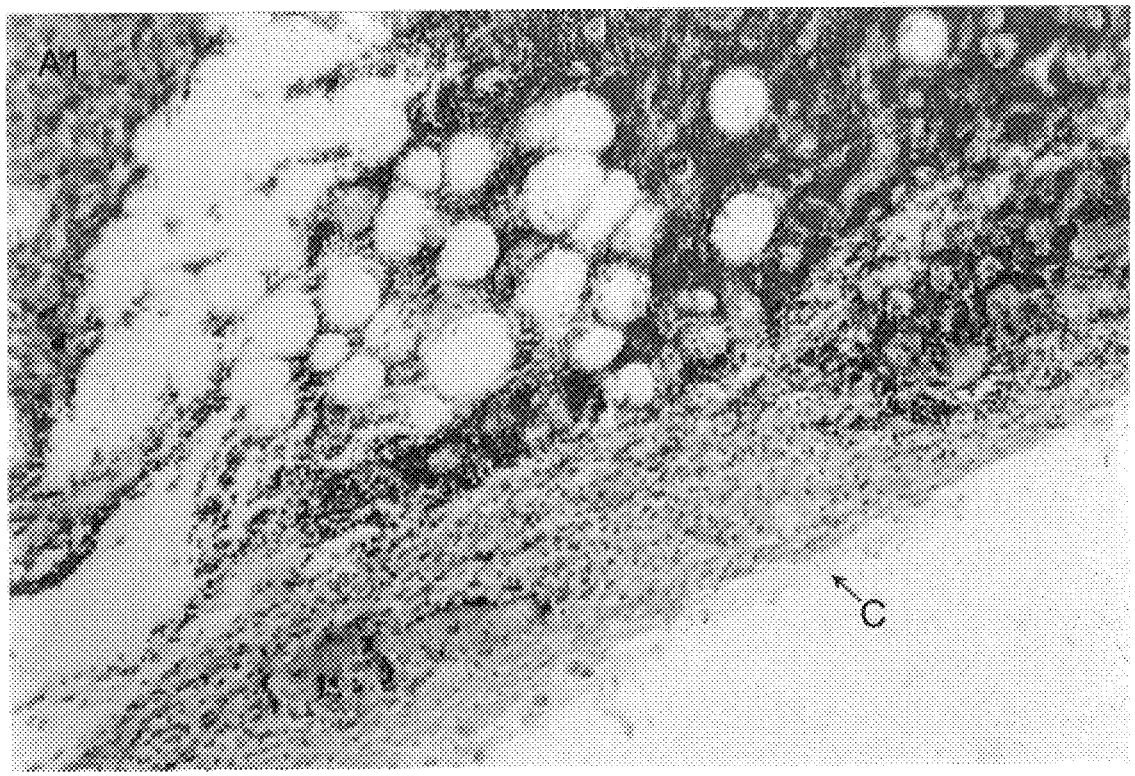
Figure A1
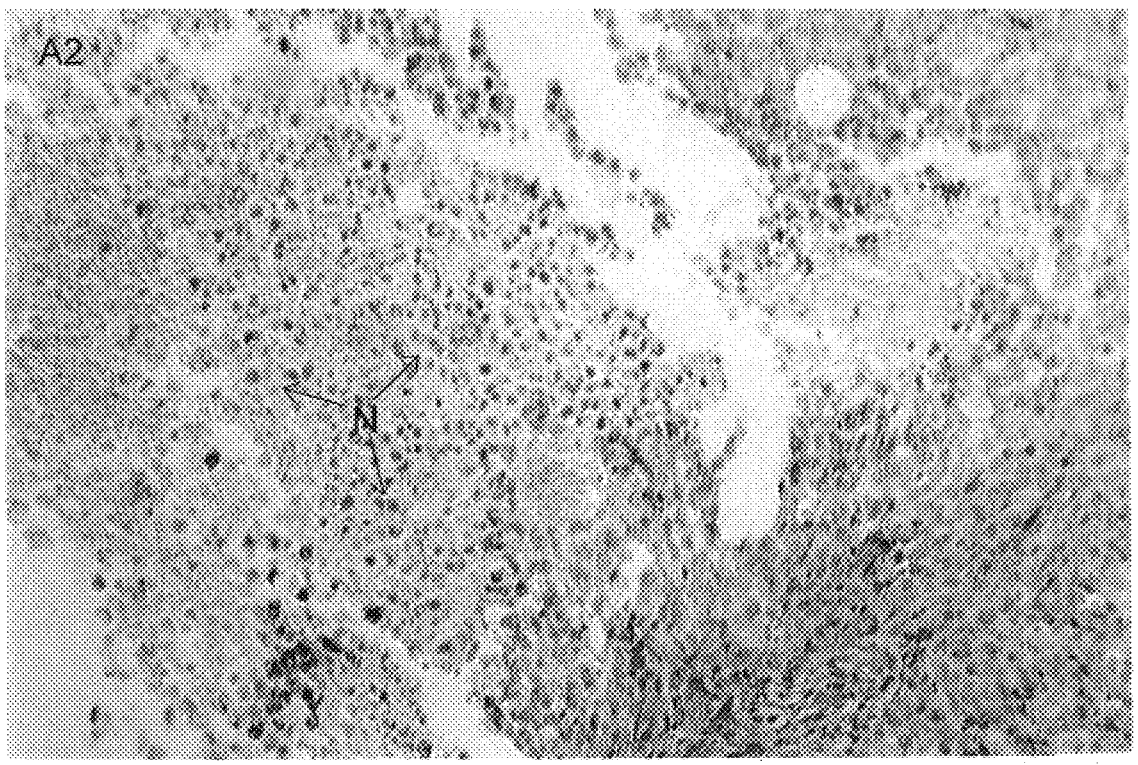
Figure A2

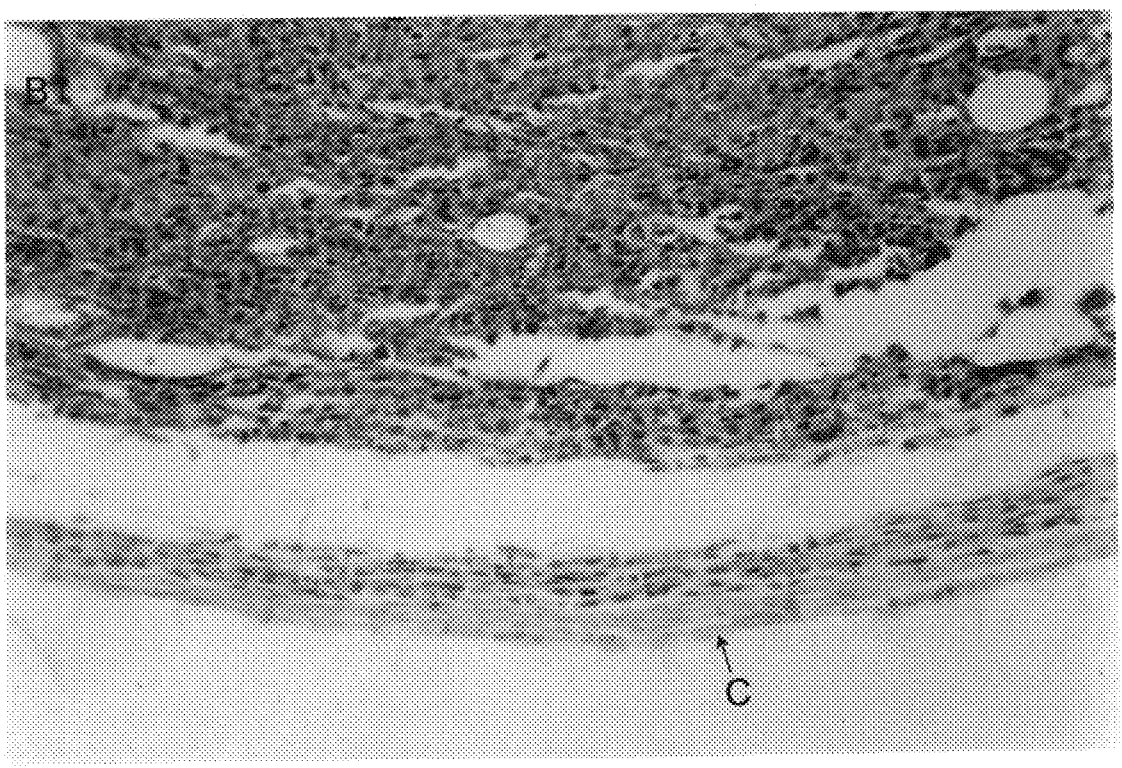
Figure B1
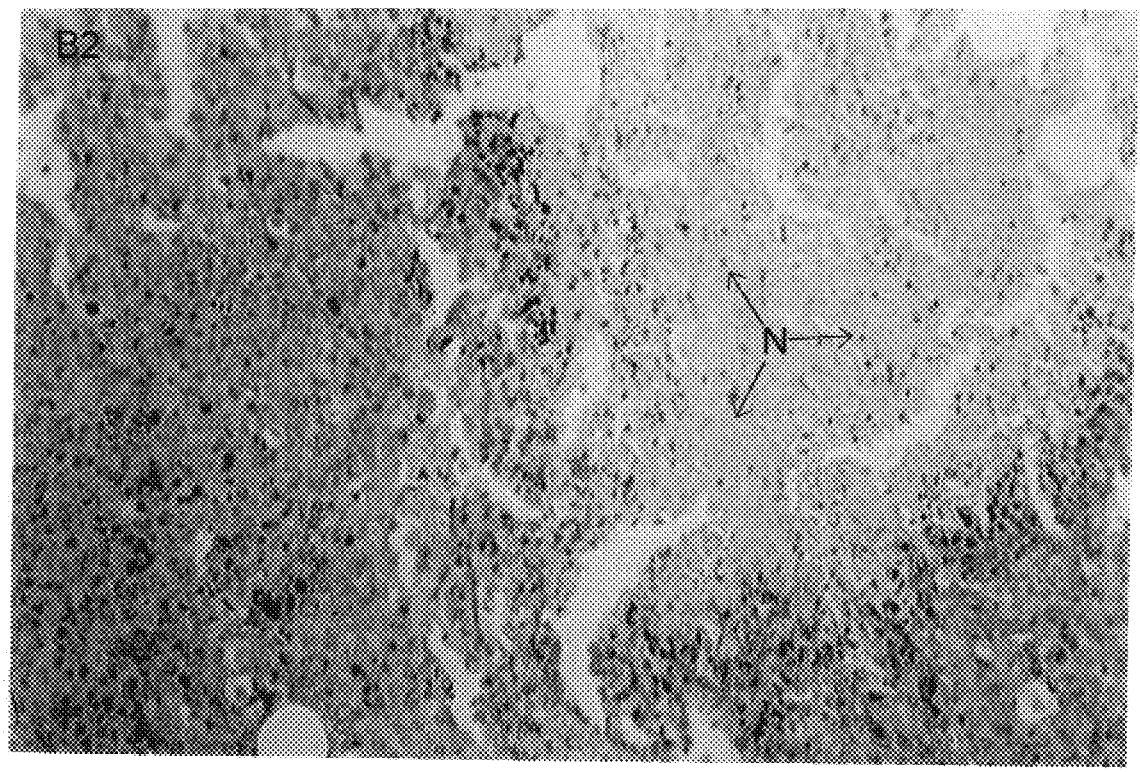
Figure B2

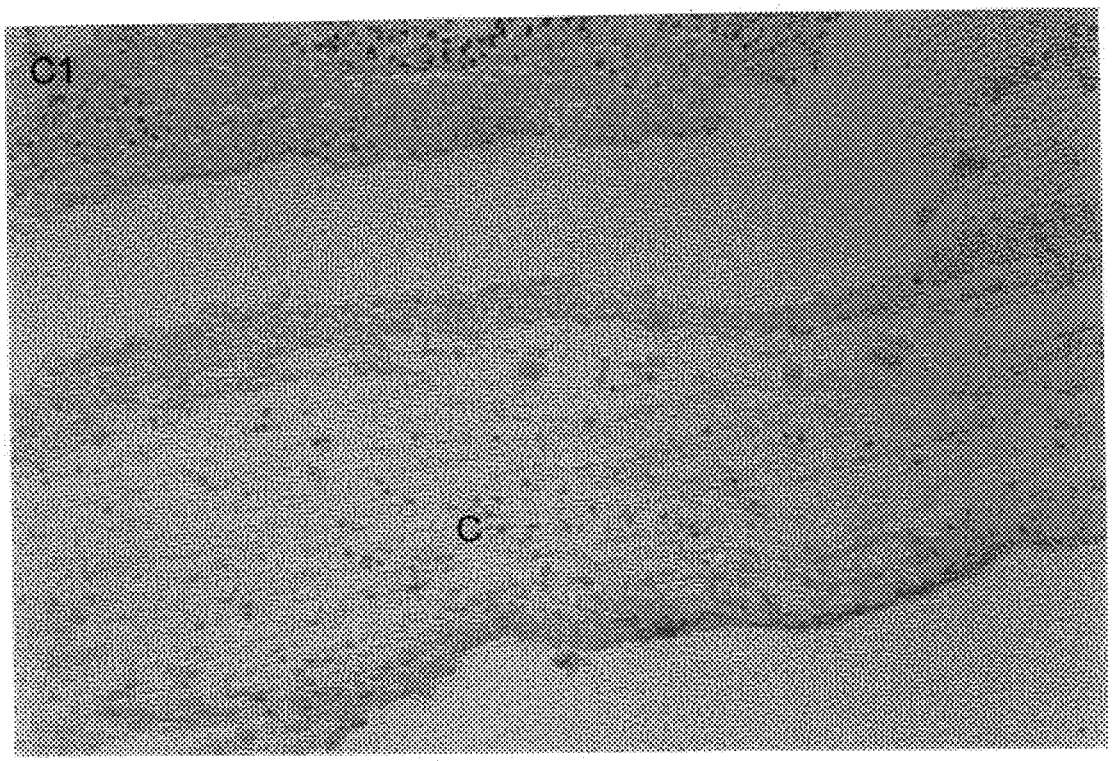
Figure C1
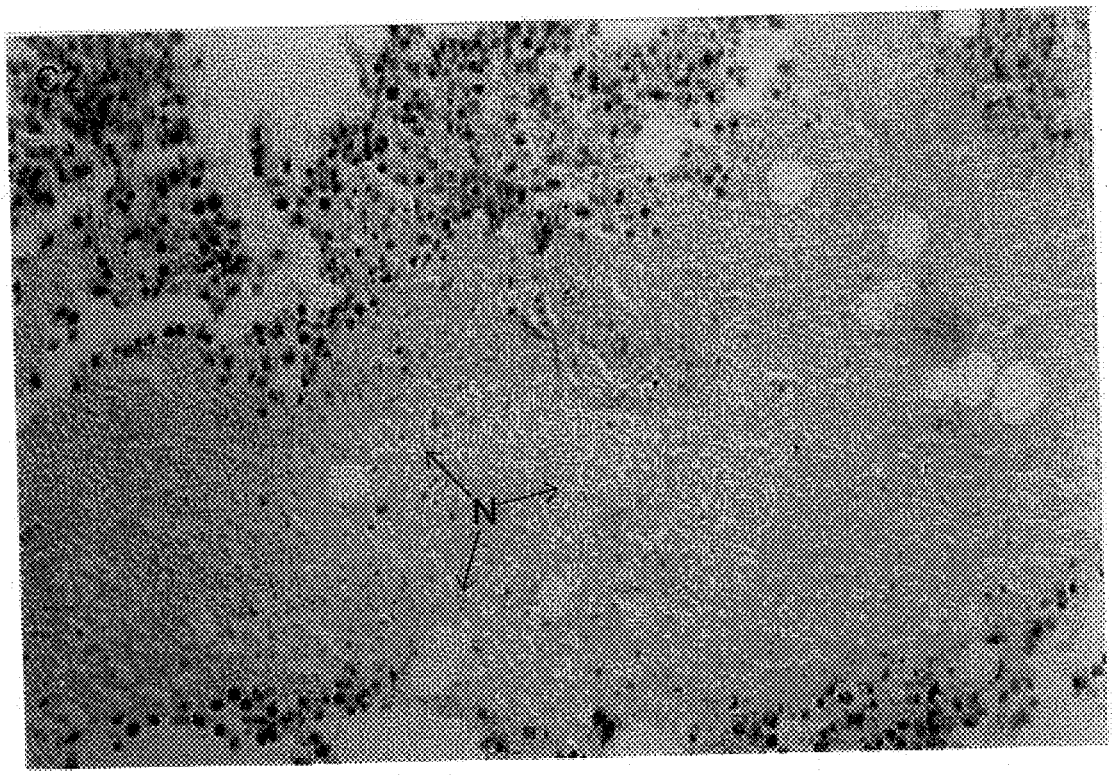
Figure C2

SALTS OF ANIONIC COMPLEXES OF RU (III), AS ANTIMETASTATIC AND ANTINEOPLASTIC AGENTS

FIELD OF THE INVENTION

The present invention relates to new salts of anionic complexes of Ru(III) with ammonium cations which are particularly useful as antimetastatic and antineoplastic agents.

STATE-OF-THE-ART

The discovery of the antineoplastic properties of cisplatin (cis-diammino-dichloro-platinum (II)), so far widely used both in antitumor mono- and polychemotherapy, has fostered the interest in the study of the antitumor activity of the metallo-organic complexes. As for many antitumor agents, the specificity of action of the cisplatin, is directed towards neoplasms which affect specific compartments (testis, ovary, bladder, head-neck), while other kinds of tumors, such as those localised in the lungs and in the breast and the colon-rectal tumor, are almost insensitive to treatment with this drug (C. F. J. Barnard et al., Chemistry in Britain, 1001–1004, 1986).

Thus, research in the field of the coordination complexes is aimed at the development of new drugs containing Pt and/or other transition elements which can enable both the enlargement of the spectrum of use and the achievement of toxicity levels lower than those of the antitumor agents which are known in the state-of-the-art.

The potentiality of the use of ruthenium as antitumor agent as an alternative to platinum was studied for complexes of Ru (II) like, for example, cis-Ru(III)-tetrakis-dimethylsulfoxide (T. Giraldi et al., Cancer Res., 37, 2662, 1977) and more recently for neutral complexes of Ru (III), such as fac-[RuCl$_3$ (NH$_3$)$_3$] (M. J. Clarke, Metal Ions in Biological Systems, 11(5), 231–281, 1980, Helmut Sigel Ed.). Moreover, several anionic complexes of Ru(III) with 5-membered heterocycles have been prepared, in particular imidazolium-bis-imidazole-tetrachloro-ruthenate (III) (B. K. Keppler et al., J. Cancer Res. Clin. Oncol., 111: 166–168, 1986).

More recently, some Ru(III) complexes with DMSO have been developed; in particular, the WO 90/13553 international patent application describes some Ru(III) complexes having the formula (i):

[Ru(R$_x$R$_y$SO)(Cl$_3$)AB]  (i)

where R$_x$R$_y$SO is a sulfoxide, preferably dimethylsulphoxide, A is a sulphoxide or a chloride and B is a nitrogen ligand, selected from the group consisting of ammonia, primary, secondary and tertiary amines, and heterocycles containing nitrogen atoms.

These complexes, which can be used as antineoplastic agents, are neutral when A is a sulfoxide, while they possess a negative charge when A is a chloride; in this latter case, the anionic complexes are isolated in the form of the corresponding salts with alkaline and alkaline earth cations and preferably sodium.

Despite their antimetastatic activity, the above mentioned complexes exhibit some serious inconveniences which make the administration and formulation in adequate therapeutical compositions extremely difficult. As a matter of fact, these anionic complexes when isolated in the form of sodium salts, always contained two solvent molecules of crystallisation and cannot be isolated in a pure form, that is without these crystallisation molecules.

In particular, the [trans-RuCl$_4$(DMSO)Im]Na 2DMSO, corresponding to formula (i) where R$_x$=R$_y$=methyl, A=Cl, B=imidazole and where the negative charge has been neutralized by Na+, is capable of exerting good antineoplastic and antimetastatic activities on tumor models in mice. Moreover, this salt has been characterised by good water solubility which allows for an easier administration.

However, this compound can be isolated only with two DMSO salvation molecules, as evidenced in the examples reported in the above mentioned international patent application (in particular, in the Examples 3, 4, 8 and 10) which reduce the compound stability.

Moreover, a qualitative variability of the crystallisation molecules, which can be DMSO, acetone and water, and more commonly two dimethylsulfoxide molecules (DMSO) (E. Alessio et al. Inorganica Chimica Acta, 203 (1993): 205–217) can be observed.

The fact that the crystallisation molecules vary in a way which is hardly controlled from one preparation to another causes problems of uncertainty in structural analysis, in the molecular weight determination and in the elemental analysis. Hence, problems related to the of the purity of the compound and its subsequent formulation may occur. As a matter of fact, the scarce structural reproducibility of these compounds implies that not always the same amount of ruthenium corresponds to the administered dose. Thus non-constant dosages and therapeutical activities that cannot easily be foreseen reduce the pharmacological interest of these compounds.

A further disadvantage of the above mentioned compound is due to pharmacological negative effects caused by DMSO, introduced in the organism in equimolar or double quantities with respect to the ruthenium complex and to its differentiating properties, as reported by Klaas Kramer et al. (Gen. Pharmac., vol. 26, n°6, pp. 1403–1497, 1995).

Finally, since the above mentioned salts contain salvation molecules, they rapidly degrade when exposed to open air at room temperature up to providing some brown semisolid substance.

SUMMARY

The Applicant has now surprisingly found new salts of Ru(III) anionic complexes with ammonium cations which exhibit a remarkable antimetastatic and antineoplastic activity. These salts correspond to formula (I):

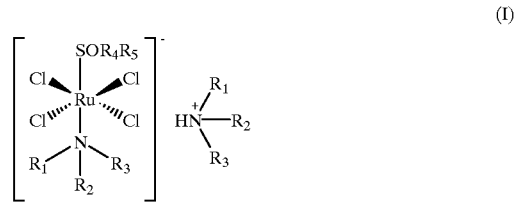

(I)

where R$_1$, R$_2$ and R$_3$, equal or different from each other, are selected from the group consisting of H, C$_1$–C$_6$ alkyl, linear or branched, saturated or unsaturated, C$_3$–C$_7$ cycloalkyl, phenyl and aryl;

or NR$_1$R$_2$R$_3$ is a 5–7 membered nitrogen containing heterocycle, saturated or unsaturated, optionally containing one or more O, S and /or N atoms, said nitrogen atom being optionally substituted with a C$_1$–C$_4$ alkyl, aryl or benzyl residue; said nitrogen containing heterocycle being optionally condensed with a benzo group and/or substituted with C$_1$–C$_4$ alkyl, C$_1$–C$_4$ alkoxyl, C$_1$–C$_4$ alkylthio, aryl or benzyl groups;

where $R_4$ and $R_5$, equal or different from each other, are selected from the group consisting of H, $C_1$–$C_6$ alkyl, $C_3$–$C_7$ cycloalkyl, phenyl and aryl or $R_4$ and $R_5$ form, together with the S atom, a 4–7 membered heterocycle.

A further object of the present invention is a new process for the preparation of the above salts (I) which comprises the synthesis of [trans-RuCl$_4$(R$_4$R$_5$SO)$_2$][(R$_4$R$_5$SO)$_2$H] (II), where $R_4$ and $R_5$ have the above meanings, which is obtained by treatment of RuCl$_3$ with R$_4$-SO-R$_5$ in the presence of HCl, and the following reaction of the complex (II) with a nitrogen containing compound of formula NR$_1$R$_2$R$_3$, in the presence of an organic solvent.

Moreover, the present invention relates to the pharmaceutical compositions containing therapeutically effective amount of at least one of the above salts of formula (I), in combination with the proper excipients and/or diluents and their use as antineoplastic and/or antimetastatic agents.

DESCRIPTION OF THE FIGURES

The file of this patent contains at least one drawing executed in color. Copies of this patent with color drawings will be provided by the Patent and Trademark Office upon request and payment of the necessary fee.

FIG. A1 and FIG. A2 respectively show the external connective capsule and a necrotic area of the tumor tissue of the control mice affected by MCa mammary carcinoma.

FIGS. B1 and B2 respectively show the external connective capsule and a necrotic area of the tumor tissue in mice affected by MCa mammary carcinoma, after treatment with [trans-RuCl$_4$(DMSO)Im]Na 2DMSO, as described in the above mentioned WO 90/13553 international patent application.

Finally, the C1 and C2 Figures exhibit the external connective capsule and a necrotic area in the tumor tissue of mice affected by MCa mammary carcinoma, after treatment with the salt [trans-RuCl$_4$(DMSO) (Im)][ImH] (Example 2) of the present invention.

DETAILED DESCRIPTION OF THE INVENTION

The features and the advantages of the present invention will be better illustrated in the course of the following detailed description.

In the above mentioned salts of formula (I), the nitrogen atom of the nitrogen compound of formula NR$_1$R$_2$R$_3$ supplies its long pair in the formation of the coordination bond with the Ru(III) atom.

More specifically, in the salts of the invention, $R_1$ is preferably the same as $R_2$ and $R_3$ and they are H or ethyl.

When NR$_1$R$_2$R$_3$ is a 5-membered nitrogen containing heterocycle, it selected from the group consisting of imidazole, N-methyl-imidazole, pyrazole, and oxazole; most preferably said nitrogen-containing heterocycle is imidazole.

When NR$_1$R$_2$R$_3$ is a 6-membered heterocycle, it is selected preferably in the group consisting of pyridine, pyrazine, 3,5-lutidine and 4-methylpyridine.

When NR$_1$R$_2$R$_3$ is a 7-membered heterocycle, it is selected from the group consisting of azepine, diazepine, and oxazepine.

Finally, when said heterocycle is condensed with a benzo group, it is selected preferably from the group consisting of indazole, isoquinoline, benzimidazole and 1,5,6-trymethyl-benzimidazole.

In the salts of the invention of formula (I), the R$_4$-SO-R$_5$ sulphoxide ligand is preferably dimethylsulfoxide (R$_4$=R$_5$= methyl), diethylsulphoxide (R$_4$=R$_5$=ethyl) or tetramethylensulphoxide (together with the S atom, $R_4$ and $R_5$ form a 5-membered ring).

These salts can unexpectedly exert an antitumor and in particular antimetastatic activity which is significantly higher than that of the corresponding sodium salts, when equimolar doses and equal treatment patterns are applied.

Moreover, the salts of formula (I), with respect to those described in the state-of-the-art, are much more favourable since they are indefinitely stable in the air, while the corresponding sodium salts, being extremely hygroscopic, are easily subject to hydrolysis. In addition to that, with respect to the known complexes, the salts of the invention do not exhibit the pharmacological drawbacks which are due to the presence of DMSO crystallisation molecules.

Since the salts of formula (I) have no crystallisation molecules, they have constant MW values as well as reproducible analytical results. This allows for formulations containing definite amounts of active compound and consistently constant dosages.

The salts of Ru(III) complexes of formula (I) are obtained by means of a new particularly easy and favourable procedure which comprises the following steps:

1) reactions of RuCl$_3$ with R$_4$-SO-R$_5$ in the presence of HCl, to produce the complex of formula (II)

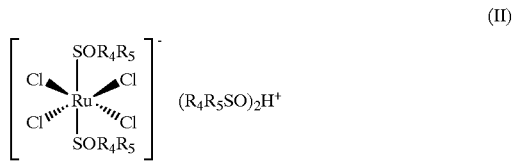

(II)

where $R_4$ and $R_5$ have the above reported meanings.

In this reaction step, $R_4$ and $R_5$ are preferably methyl, that is RuCl$_3$ undergoes reaction with dimethylsulfoxide (DMSO) to produce [(Me$_2$SO)$_2$H][trans-RuCl$_4$(Me$_2$SO)$_2$].

According to a preferred way of preparation, RuCl$_3$ is previously dissolved in a heated organic solvent, preferably ethanol or methanol; R$_4$-SO-R$_5$ and concentrated HCl are added to the solution obtained in this way and heated at a temperature ranging preferably from 60 and 90° C., and even more preferably at a temperature of about 80° C.

2) The complex (II), obtained from step (1), is reacted at room temperature with a NR$_1$R$_2$R$_3$ nitrogen containing compound, in molar ratios ranging from 1:2 to 1:6 in one or more organic solvents, preferably acetone and dichloromethane, to provide the salts of formula (I), according to the scheme reported hereunder:

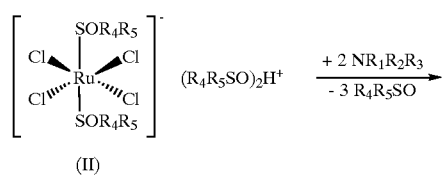

(II)

-continued

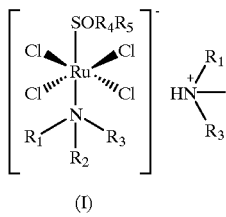

(I)

where $R_1$–$R_5$ have the previously defined meanings.

In the step (2), the intermediate (11) reacts with the $NR_1R_2R_3$ nitrogen containing compound by leading to the replacement of one of the two axial sulphoxide groups and to the protonation of a molecule of the nitrogen compound and to the final release of two sulphoxide crystallisation molecules. Thus the complexes (I) are obtained in very high yields.

A further object of the present invention is the use of the above salts (I) in the treatment of neoplasms of a various nature and in the prevention of the formation of metastases. The above neoplasms are preferably solid spawning tumors, such as the carcinoma of the gastrointestinal tract, the mammary carcinoma, the lung tumors, the metastatic carcinoma and the lung metastases of metastatic tumors. The salts of the invention can be profitably administered by parenteral, oral, topical or transdermal route.

Among the parenteral administration, the intravenous, intramuscular, intraperitoneal and subcutaneous routes are preferred.

The dosage of these salts varies according to the route and ways of administration as well as to the seriousness of the neoplasms; besides, it varies in relation to age, to the body weight and to the general healthiness of the patient.

The therapeutically effective dose of these salts, to be administered in single or multiple doses, ranges preferably from 0.1 to 300 mg/kg/day and even more preferably is 10–200 mg/kg/day, when these salts are administered parenterally, while orally the dosages are from 3 to 10 times higher than the above reported range.

Moreover, the above salts (I) can profitably be used in experimental protocols of polychemotherapy in combination with other antitumor drugs of common clinical use in the above described pathologies, such as for example cisplatin, 5-fluorouracil, vinblastin, cyclophosphamide, bleomycin, anthracycline, taxol.

The present invention also relates to pharmaceutical compositions containing, as an active compound, a therapeutically effective amount of at least one salt of formula (I) in combination with suitable excipients and/or diluents.

These pharmaceutical compositions can be prepared in the form of solutions or suspensions, both in aqueous and non-aqueous media, which are particularly suitable for intravenous injections, infusions and intramuscular or subcutaneous injections. These solutions can be prepared before use, by solubilizing or suspending the lyophilized compounds of the invention in suitable solvents.

Solid or semisolid compositions in the form of inserts, gels or ointments for topical, dermal or transdermal administration or in the form of powder, pills, tablets, and capsules are also indicated. Furthermore, the salts of the invention can be administered in the form of controlled-release compositions which are known in the state-of-the-art.

The above compositions can be prepared easily according to procedures which are known in the state-of-the-art.

The following examples are reported to illustrate the invention without limiting it:

EXPERIMENTAL PART

EXAMPLE 1

Preparation of [trans-RuCl$_4$(Me$_2$SO)$_2$][(Me$_2$SO)$_2$H] Complex Corresponding to Formula (II) where $R_4$=$R_5$=methyl.

1 g of RuCl$_3$ 3 H$_2$O (0.0038 moles) was suspended in 30 ml ethanol and underwent reflux heating for three hours to obtain a dark green solution. The solution was filtered on paper to remove possible traces of undissolved solid; it was then concentrated by using a rotary evaporator up to ⅒ of the initial volume; therefore, 1 ml of aqueous concentrated HCl, 37% and 2 ml of DMSO were added and the mixture obtained in this way was kept at a temperature of 80° C. for about 15 minutes, up to obtaining a bright orange solution.

After cooling of the mixture to room temperature and after addition of 10 ml acetone, the product, after setting up, separated from the solution in the form of red-orange crystals; the formation of these crystals was accelerated by the addition of a few drops of ethyl ether. The crystals were then collected on a filter, washed with cold acetone (20 ml), then with ethyl ether (10 ml) and finally dried under vacuum at room temperature. 1.5 g of the final product with a 72% yield was obtained.

The physico-chemical features of [trans-RuCl$_4$(Me$_2$SO)$_2$][(Me$_2$SO)$_2$H] are as follows:

physical state: a red-orange, crystalline solid
raw formula: $C_8H_{25}Cl4O_4RuS_4$
molecular weight: 556.40
elemental analysis:
experimental: C=17.33, H=4.61 Cl=25.2 S=23.2
theoretical: C=17.27, H=4.53 Cl=25.48 S=23.04

Moreover, the IR and UV spectra and the determination of the structure by means of X-rays turned out to be in agreement with what reported by E. Alessio et al. (above mentioned reference).

EXAMPLE 2

Preparation of [trans-RuCl$_4$(DMSO) (Im)][ImH] Corresponding to Formula (I) where $NR_1R_2R_3$ is Imidazole (Im) and $R_4$=$R_5$=methyl.

1.0 g (0.0018 moles) of the [trans-RuCl$_4$(Me$_2$SO)$_2$][(Me$_2$SO)$_2$H] complex prepared as described in Example N.1, was suspended in acetone (20 ml) at room temperature.

After the addition of 0.49 g (0.0072 moles) of imidazole, the mixture was kept under stirring for 4 hours; during this time the colour of the precipitate gradually changed from orange to brick red. After being collected on a filter and washed with acetone (10 ml) and therefore with ethyl ether (10 ml), the product was dried under vacuum at room temperature or in a oven at 60° C. for a few hours. Hence, 0.75 g of final product were obtained with a 92% yield.

The physico-chemical properties of [trans-RuCl$_4$(DMSO) (Im)][ImH] are as follows:

physical state: a brick-red crystalline solid
raw formula: $C_8H_{15}N_4Cl_4ORuS$
molecular weight: 458.17
elemental analysis:
experimental: C=20.8, H=3.30 N=12.2
theoretical: C=20.87, H=3.30 N=12.23
1 H-NMR spectrum in D20 (ppm vs DSS):–15.2 (Very broad, DMSO), 3.53 (broad, H2 Im), 7.48 (2, H3 and 4H ImH$^+$), 8.70 (1, H2 ImH$^+$);

IR spectrum (selected frequencies, Nujol, cm-1): $v_{NH}$ 3150 (very broad, medium), $v_{SO}$ 1159 (very strong), vRu-S 421 (medium), vRu-Cl 342 (strong).

EXAMPLE 3

Preparation of [trans-RuCl$_4$(DMSO) (1-Me-Im)][1-Me-ImH] Corresponding to Formula (I) where NR$_1$R$_2$R$_3$ is 1-methyl-imidazole and R$_4$=R$_5$= methyl.

1.0 g (0.0018 moles) of the [trans-RuCl$_4$(Me$_2$SO)$_2$][(Me$_2$SO)$_2$H] complex prepared as described in Example N.1, was treated with 0.59 g (0.0072 moles) of 1-methylimidazole as described in Example N.2, and 0.8 g of final product were obtained in a 93% yield.

The physico-chemical properties of the [trans-RuCl$_4$(DMSO)(1-Me-Im)][1-Me-ImH] are as follows:

physical state: a brick-red crystalline solid raw formula: C$_{10}$H$_{19}$N$_4$Cl$_4$ORuS molecular weight: 486.23 elemental analysis:

experimental: C=24.8, H=3.83 N=11.4 theoretical: C=24.7, H=3.94 N=11.52

1 H-NMR spectrum in D$_2$O (ppm vs DSS): −15.7 (Very broad, DMSO), 3.76 (broad, H2 1-Me-Im), −0.95 (broad, Me1, 1-Me-Im) 3.95 (3, Me1, 1-Me-ImH$^+$), 7.45 (2, H3 and H4 1-Me-ImH$^+$), 8.68 (1, H2 1-Me-ImH$^+$);

IR spectrum (selected frequencies, Nujol, cm$^{-1}$): $v_{NH}$ 3150 (very broad, medium), $v_{SO}$ 1093 (very strong), vRu-S 424 (medium), v Ru-Cl 326 (strong).

EXAMPLE 4

Preparation of [trans-RuCl$_4$(DMSO)(Py)][PyH] Corresponding to Formula (I) where NR$_1$R$_2$R$_3$ is Pyridine and R$_4$=R$_5$=methyl.

1.0 g (0.0018 moles) of the [trans-RuCl$_4$(Me$_2$SO)$_2$][(Me$_2$SO)$_2$H] complex prepared as described in Example 1, was treated with 0.57 g (0.0072 moles) of pyridine as described in Example 2. 0.8 g. of the final product were obtained with a 94% yield.

The physico-chemical features of the [trans-RuCl$_4$(DMSO) (Py)][PyH] are as follows:

physical state: a dark yellow microcrystalline solid raw formula: C$_{12}$H$_{17}$N$_2$Cl$_4$ORuS molecular weight: 480.22 elemental analysis:

experimental: C=31.8, H=3.77 N=5.43 theoretical: C=30.01 H=3.57 N=5.83

$^1$H-NMR spectrum in D$_2$O (ppm vs DSS): −14.5 (Very broad, DMSO), 2.90 (broad, Py), 8.10, 8.65, 8.82 (PyH$^+$);

IR spectrum (selected frequencies, Nujol, cm$^{-1}$): vNH 3150 (very broad, medium), vSO 1074 (very strong), v Ru-S 432 (medium), v Ru-Cl 344 (strong).

EXAMPLE 5

Preparation of [trans-RuCl$_4$(DMSO)(NH$_3$)][NH$_4$] Corresponding to Formula (I) where NR$_1$R$_2$R$_3$ is NH$_3$ and R$_4$=R$_5$=methyl.

1.0 g (0.0018 moles) of the [trans-RuCl$_4$(Me$_2$SO)$_2$][(Me$_2$SO)$_2$H] complex prepared as described in Example 1, was suspended in CH$_2$Cl$_2$ (20 ml) at room temperature after creating vacuum by a water pump, gaseous NH$_3$ was bubbled and the system obtained in this way was kept under stirring for 4 hours, at room temperature, under ammonia atmosphere; during this time, the colour of the precipitate gradually passed from orange to dark red.

The product collected on a filter and washed with cold CH$_2$Cl$_2$ and then with ethyl ether (10 ml), was then dried under vacuum at room temperature.

The physico-chemical features of [trans-RuCl$_4$(DMSO)(NH$_3$)][NH$_4$] are as follows:

physical state: brick red microcrystalline solid raw formula: C$_2$H$_{13}$N$_2$Cl$_4$ORuS molecular weight: 356.08 elemental analysis:

experimental: C=6.75 H=3.44 N=7.63 theoretical: C=6.75 H=3.68 N=7.87

IR spectrum (selected frequencies, Nujol, cm$^{-1}$): vNH 3304, 3174 (medium), vSO 1069 (very strong), vRu-N 458 (weak), vRu-S 431 (medium), vRu-Cl 334, 321 (strong).

EXAMPLE 6

Preparation of [trans-RuCl$_4$(DMSO) (Pyr)][PyrH] Corresponding to Formula (I) where NR$_1$R$_2$R$_3$ is Pyrazine (Pyr) and R$_4$=R$_5$=methyl.

1.0 g (0.0018 moles) of the [trans-RuCl$_4$(Me$_2$SO)$_2$][(Me$_2$SO)$_2$H] complex prepared as described in Example N.1, was treated with 0.43 g (0.0053 moles) of pyrazine as described in Example N.2, and 0.5 g of final product were obtained in a 57% yield.

The physico-chemical properties of the [trans-RuCl$_4$(DMSO) (Pyr)][PyrH] are as follows:

physical state: a dark yellow crystalline solid raw formula: C$_{10}$H$_{15}$N$_4$Cl$_4$ORuS molecular weight: 482.20 elemental analysis:

experimental: C=24.7, H=3.07 N=11.1 theoretical: C=24.9, H=3.13 N=11.6

1H-NMR spectrum in D$_2$O (ppm vs DSS): −13.8 (broad, DMSO), −7.5 (very broad, H2.6 Pyr), −2.1 (broad, H3.5 Pyr) 8.69 (Pyr)

IR spectrum (selected frequencies, Nujol, cm$^{-1}$): vPyrazine 1605 (medium), vSO 1076 (very strong), vPyrazine 807 (strong), vProtonated pyrazine 773 (strong), vRu-S 435 (medium), v Ru-Cl 351,326 (strong).

UV/VIS in water (nm, ε (mol-1 cm−1): 400 (4200), 469 (490).

BIOLOGICAL ACTIVITY i) In vivo Activity Test of the Salts (I), according to the Present Invention, on Mice affected by Lewis Lung Carcinoma.

Example (i)-A

Materials and methods

Three groups, each made up of 10 female BD2F1 mice of 21±1 g, obtained from Charles River (Calco, Como, Italy) were inoculated by intramuscular injection, with 10$^6$ Lewis lung carcinoma cells suspended in 0.05 ml of a Dulbecco's buffered calcium and magnesium-free solution (PBS) using a sterile insulin syringe.

The tumor line was obtained by the Tumor Repository Bank, NCl, NlH, Bethesda (USA) and maintained in liquid nitrogen.

Five days after the above inoculation, the average weight of the tumor was equal to 0.4±0.01 g. From the 5th to the 11th day, the three groups of mice were treated intraperitoneally as follows:

Group 1—Control: 10 ml/kg of body weight/day of a sterile and pyrogen-free physiological solution;

Group 2—10 ml/kg of body weight/day of a sterile and pyrogen-free physiological solution containing 44 mg of [trans-RuCl$_4$(DMSO) (Im)]Na 2DMSO, as described in the above mentioned WO 90/13553 international patent application;

Group 3—10 ml/kg of body weight/day of a sterile and pyrogen-free physiological solution containing 35 mg of [trans-RuCl$_4$(DMSO) (Im)][ImH] (Example 2);

12 days after inoculation, the primary tumor was surgically removed.

21 days after inoculation, the mice were sacrificed by cervical dislocation and the lung metastases were counted. The lungs were abducted immediately after death of the mice and were divided in single lobes, which were then subsequently examined by the use of a low magnification stereoscopic microscope, equipped with a grid on the eyepiece, which allowed the detection of a and b orthogonal axes (where a≦b).

The lung metastases were then classified according to their dimensions and the weight of the metastases for each animal was then calculated as the sum of the weight of each single metastases, each one regarded as a solid by means of the formula $(\pi/6)$ a$^2$×b. The experimental data obtained were then processed with the Student-Newmann-Keuls statistical test.

The results obtained are hereunder reported in Table 1, where the number of metastases and their weight in both groups of treated mice (2) and (3) are reported with respect to the control Group (1). The figures are reported as the average ±S. E. of the single values obtained for each group.

Table 1: Antitumor and antimetastatic activity on mice affected by Lewis lung carcinoma, of [trans-RuCl$_4$(DMSO) (Im)][ImH] of Example 2 (35 mg/kg/day) with respect to the [trans-RuCl$_4$(DMSO) (Im)]Na 2DMSO (44mg/kg/day).

| Compound | N ° of metastases for each animal | weight of metastases for each animal |
| --- | --- | --- |
| control | 28,9 ± 5,2 | 16,3 ± 5,2 |
| [trans-RuCl$_4$(DMSO) (Im)]Na 2DMSO | 11,9 ± 2,2* | 2,8 ± 0,8* |
| [trans-RuCl$_4$(DMSO) (Im)][ImH] | 8,8 ± 1,3* | 2,2 ± 0,3* |

*p < 0.05 with repect to the control group; test-t for grouped data.

The figures reported above outline the fact that the treatment with [trans-RuCl$_4$(DMSO) (Im)][ImH] according to the present invention causes a reduction both in the weight and in the number of metastases which is higher than the one obtained with the reference compound known in the state of the art.

The % reduction in the number of metastases and in their weight is hereunder reported in Table 2.

Table 2: % reduction in the number of metastases and in their weight in mice affected by Lewis lung carcinoma and treated with the compounds according to the present invention.

| compound | (%) reduction in the N ° of metastases | (%) reduction in the N ° of metastases |
| --- | --- | --- |
| [trans-RuCl$_4$(DMSO) (Im)]Na 2DMSO | 58,3 | 83,0 |
| [trans-RuCl$_4$(DMSO) (Im)][ImH] | 69,1 | 86,4 |

The advantages obtained with the compound of the invention with respect to the reference compound, as known in the state-of-the-art, are pointed out even more neatly by the figures reported above.

After the above treatments, the lung metastases isolated from the groups (1) and (3) of mice were counted and divided in three groups according to the diameter dimensions (d): metastases with a diameter d<1 mm (small), metastases with a a diameter ranging from 1 mm and 2 mm (medium) and finally metastases with a diameter d>2 mm (large). The results obtained are hereunder reported in Table 3.

Table 3: distribution according to diameter dimensions (d) of lung metastases in mice affected by Lewis lung carcinoma, treated with the compounds of the present invention.

| Compound | d < 1 mm metastases | 1 m < d < 2 mm metastases | d < 2 mm metastases |
| --- | --- | --- | --- |
| control | 68,4% | 29,8% | 1,8% |
| [trans-RuCl$_4$(DMSO) (Im)][ImH] | 83,0% | 17,0% | 0% |

These figures outline the fact that metastatic nodules of medium and large dimensions in the group of animals treated are scarcely present (nodules of medium dimensions) or absent (nodules of large dimension) with respect to the controls.

Example (i)-B

Materials and methods

Three groups, each made up of 10 female BD2F1 mice of 21±1 g, obtained from Charles River (Calco, Como, Italy) were inoculated by intramuscular injection, with 10$^6$ Lewis lung carcinoma cells suspended in 0.05 ml of a Dulbecco's buffered calcium and magnesium-free solution (PBS) using a sterile insulin syringe. The tumor line was obtained by the Tumor Repository Bank, NCl, NlH, Bethesda (USA) and maintained in liquid nitrogen.

Five days after the above inoculation, the average weight of the tumor was equal to 0.4±0.01 g. From the 12th to the 17th day, the three groups of mice were treated intraperitoneally as follows:

Group 1—Control: 10 ml/kg of body weight/day of a sterile and pyrogen-free physiological solution;

Group 2—10 ml/kg of body weight/day of a sterile and pyrogen-free physiological solution containing 2 mg of Cisplatin Group 3—10 ml/kg of body weight/day of a sterile and pyrogen-free physiological solution containing 35 mg of [trans-RuCl4(DMSO) (Im)][ImH] (Example 2).

11 days after inoculation, the primary tumor was surgically removed.

25 days after inoculation, the mice were sacrificed by cervical dislocation and the lung metastases were counted. The lungs were abducted immediately after death of the mice and were divided in single lobes, which were then subsequently examined by the use of a low magnification stereoscopic microscope, equipped with a grid on the eyepiece, which allowed the detection of a and b orthogonal axes (where a<b).

The lung metastases were then classified according to their dimensions and the weight of the metastases for each animal was then calculated as the sum of the weight of each single metastases, each one regarded as a solid by means of the formula $(\pi/6)$ $a^2 \times b$. The experimental data obtained were then processed with the Student-Newmann-Keuls statistical test.

The results obtained are hereunder reported in Table 4, where the number of metastases and their weight in both groups of treated mice (2) and (3) are reported with respect to the control Group (1). The figures are reported as the average ±S. E. of the single values obtained for each group.

Table 4: Antimetastatic activity on mice affected by Lewis lung carcinoma, of [trans-RuCl$_4$(DMSO) (Im)][ImH] of Example 2 (35 mg/kg/day) with respect to Cisplatin (2mg/kg/day).

| compound | N° of lung metastases | weight of lung metastases (mg) |
| --- | --- | --- |
| control | 14,8 ± 0,6 | 985,0 ± 41.0 |
| [trans-RuCl$_4$(DMSO) (Im)][ImH] | 4,3 ± 0,5* | 73,3 ± 20,0* |
| Cisplatin | 13,5 ± 0,6* | 865,1 ± 72.8* |

*P < 0.05 vs controls and vs cisplatin; test-t for grouped data.

The figures reported above outline the fact that the treatment with [trans-RuCl$_4$(DMSO) (Im)][ImH] according to the present invention causes a reduction both in the weight and in the number of metastases which is higher than the one obtained with the reference compound.

ii) In vivo Activity Test of the Compounds of the Invention in Mice Affected by MCa Mammary Carcinoma EXAMPLE (ii)-A Materials and Methods Three groups of 7 female CBA mice of 23±2 g, obtained from a colony grown according to the procedures for kin animals. The colony obtained originally from Chester Beatthy Institute of London, was subsequently kept by means of serial couplings between kins (brother and sister) in a ratio ranging from 1:1 to 1:4. The couplings took place at the peak of the sexual maturity of the animals born in the 5th week. Animals underweight or with evident organic anomalies were discarded. The three groups were inoculated by intramuscular injection, with $_{10}6$ Lewis lung carcinoma cells suspended in 0.05 ml of a Dulbecco's buffered calcium and magnesium-free physiological solution (PBS) using a sterile syringe.

The tumor line was obtained from Rudjer Boskovic Institute and maintained in liquid nitrogen.

13 days after inoculation, the average tumor weight was 1.2±0.2 g. From day 13 to 18, the three groups of mice were treated intraperitoneally as follows:

Group 1—Control: 10 ml/kg of body weight/day of a sterile and pyrogen-free physiological solution;

Group 2—10 ml/kg of body weight/day of a sterile and pyrogen-free physiological solution containing 44 mg of [trans-RuCl$_4$(DMSO) (Im)]Na 2 DMSO, as described in the above mentioned WO 90/13553 international patent application;

Group 3—10 ml/kg of body weight/day of a sterile and pyrogen-free physiological solution containing 35 mg of [trans-RuCl$_4$(DMSO) (Im)][ImH] (Example 2).

19 days after inoculation, the primary tumor was surgically removed.

27 days after inoculation, the mice were sacrificed by cervical dislocation and the lung metastases were then counted, as described in the test (i).

The experimental figures obtained were then processed according to Student-Newmann-Keuls statistical test.

In order to evaluate the activity of the salts of the invention, the primary tumor was removed surgically from the mice in the three above groups and dissected. One tumor for each group was selected in a random way and 10 sections/tumor obtained in such a way to evaluate the whole neoplastic mass. The tumor slices were fixed in 10% formaline, embedded in paraffin and stained with the Cajal-Gallego dye in order to evidence the epithelial cells, the connective matrix and the presence of erythrocytes. The infiltration was evaluated by observing the degranulation of the polymorphonucleates (PMN) as well as the presence of apoptotic bodies.

Results:

The results obtained are reported in Table 5, where the number of metastases and their weight obtained in the groups (2) and (3) with respect to the control group (1). The figures were expressed as the average ±S. E. of the single values obtained for each group.

Table 5: antitumor and antimetastatic activity of [trans-RuCl$_4$(DMSO) (Im)][ImH] in Example 2 (35 mg/kg/day) with respect to [trans-RuCl$_4$(DMSO) (Im)]Na 2 DMSO (44 mg/kg/day) on mice affected by MCa mammary carcinoma,.

| compound | N° of metastases for each animal | weight of metastases for each animal |
| --- | --- | --- |
| control | 39,2 ± 8,1 | 31,4 ± 10,2 |
| [trans-RuCl$_4$(DMSO) (Im)]Na 2DMSO | 35,2 ± 5,5 | 8,0 ± 2,5* |
| [trans-RuCl$_4$(DMSO) (Im)][ImH] | 6,8 ± 2,2* | 0,5 ± 0,2** |

*p < 0,05 with repect to the control group; test-t for grouped figures;.
**p < 0,05 with repect to the control group and p < 0,05 with respect to the group (2) treated with [trans-RuCl$_4$(DMSO) (Im)]Na 2DMSO; test-t for grouped figures. The percentage of reduction in the number of metastases and in their weight, obtained with the compound of the invention and with the sodium salt known in the state-of-the-art with respect to the control, are hereunder reported in Table 6.

Table 6: % reduction in the number of metastases and in their weight obtained with the compounds according to the present invention.

| Compound | (%) reduction in the N° of metastases | (%) reduction in the weight of metastases |
| --- | --- | --- |
| [trans-RuCl$_4$(DMSO) (Im)]Na 2DMSO | 10,2 | 74,5 |
| [trans-RuCl$_4$(DMSO) (Im)][ImH] | 82,6 | 98,4 |

The results related to the effect of the salts of the invention are hereunder reported in Table 7.

Table 7: Effects of the compounds according to the present invention on the primary tumor.

| | Control | [trans-RuCl$_4$(DMSO) (Im)]Na 2DMSO, 44 mg/kg/day | [trans-RuCl$_4$(DMSO) (Im)][ImH] 35 mg/kg/day |
|---|---|---|---|
| Hemorrhagic areas | limited | discrete | numerous and very wide |
| Necrotic areas | limited | discrete | very wide |
| Infiltration status | high, intact PMNs | high, with partially degranulated PMNs and some apoptotic bodies | neat PMN degranulation; plenty of apoptotic bodies |
| Connective Capsule | normal, with muscular bundles which are not always intact | limited in thickness and badly distinguished from the muscular layer | wide, thick and infiltrating the tumor tissue |

From the figures reported above it is possible to detect that the [trans-RuCl$_4$(DMSO) (Im)][ImH] compound, with respect to the [trans-RuCl$_4$(DMSO) (Im)]Na 2DMSO reference compound, 44 mg/kg/day, causes profound hystologic modifications. In particular, the tumor treated with the salt according to the present invention has wide hemorrhagic and necrotic areas combined with neutrophilic leukocytes, a neat degranulation of the polymorphonucleates (PMN), the presence of a large number of apoptoptic bodies and the thicknening of the connective capsule surrounding the tumor.

These results are even more evident in the figures where the outer connective capsule is labelled with a C letter (FIGS. A1, B1 and C1), while the necrotic area is labelled with the N letter (FIGS. A2, B2 and C2).

Without meaning to restrict the mechanism of action with which the salts according to the present invention exert their pharmacological effects, the above observations contribute to explain, at least partially, the antimetastatic effect of the above salts as the result of the prevention of the tumor cell spawning from the primary tumor.

Example (ii)-B
Materials and methods

Two groups of 12 and one group of 14 (controls) female CBA mice of 22 g obtained from a colony grown according to the procedures for kin animals were inoculated with 10$^6$ cells of MCa mammary carcinoma, as reported in the test (ii)-A.

From the 9th to the 14th day since the inoculation, the three groups of mice were daily treated intraperitoneally as follows:

Group 1—Control: 10 ml/kg of body weight/day of a sterile and pyrogen-free physiological solution;

Group 2—10 ml/kg of body weight/day of a sterile and pyrogen-free physiological solution, containing 35 mg of [trans-RuCl$_4$(DMSO) (Im)][ImH] (Example 2);

Group 3—10 ml/kg of body weight/day of a sterile and pyrogen-free physiological solution containing 27 mg of [trans-RuCl$_4$(DMSO) (NH$_3$)]NH$_4$ (Example 5).

On day 27 from inoculation, the rats were sacrificed by cervical dislocation and the lung metastases were then counted, as described in the test (i).

The experimental figures obtained were then processed according to the Student-Newmann-Keuls statistical test.

In order to evaluate the activity of the salts of the invention on the primary tumor, the average weight of the primary tumor was assessed at the beginning and in the end of the above treatment.

Results:

The results obtained are reported in Table 8, where the number of metastases and their weight obtained in the groups (2) and (3) with respect to the control group (1) are shown. The figures are expressed as the average ±S. E. of the single values obtained for each group.

Table 8: antitumor and antimetastatic activity of [trans-RuCl$_4$(DMSO) (Im)][ImH] in Example 2 (35 mg/kg/day) and of the [trans-RuCl$_4$(DMSO) (NH$_3$)]NH$_4$ described in Example 5 (27 mg/kg/day) on mice affected by MCa mammary carcinoma,

| compound | N° of metastases for each animal | weight of metastases for each animal |
|---|---|---|
| control | 40,4 ± 6,0 | 115,0 ± 22,1 |
| [trans-RuCl$_4$(DMSO) (Im)][ImH] | 20,7 ± 4,0* | 23,2 ± 7,2** |
| [trans-RuCl$_4$(DMSO) (Im)] (NH$_3$)] NH$_4$ | 15,6 ± 3,2* | 10,7 ± 2,2** |

*p < 0,05 and **p < 0,01 with respect to the control group; test-t for grouped figures; The reduction percentages of the number of metastases and of their weight, obtained with the compound of the invention and with the sodium salt known in the state-of-the-art with respect to the control, are hereunder reported in Table 9.

Table 9: % reduction of the number of metastases and of their weight, obtained with the compounds according to the present invention.

| compound | % reduction of the number of metastases | % reduction of the weight of metastases |
|---|---|---|
| [trans-RuCl$_4$(DMSO) (Im)][ImH] | 48,8 | 79,8 |
| [trans-RuCl$_4$(DMSO) (Im)] (NH$_3$)] NH$_4$ | 61,4 | 90,7 |

The results related to the effect of the salts of the invention on the growth of the primary tumor are reported in Table 10, where the weight of the primary tumor at the beginning and in the end of the treatment with the salts of the invention, as well as the corresponding percentage of growth.

Table 10: effect exerted by the compounds according to the present invention on the growth of the primary tumor in mice affected by MCa mammary carcinoma.

| | weight of the primary tumor (mg) | | |
|---|---|---|---|
| compound | beginning of treatment | end of treatment | (%) growth |
| Control | 157 ± 16 | 723 ± 98 | +461 |
| [trans-RuCl$_4$(DMSO) (Im)][ImH] | 152 ± 19 | 282 ± 61** | +185 |
| [trans-RuCl$_4$(DMSO) (Im)] (NH$_3$)] NH$_4$ | 191 ± 23 | 490 ± 91* | +256 |

*p < 0,05 and **p < 0,01 with respect to the control group; t-test for grouped data. From the figures reported above, the reduction of the growth of the primary tumor in the groups treated with the salts according to the present invention, as normalized by the controls, is 59,9% for [trans-RuCl$_4$(DMSO) (Im)] [ImH], while it is 44,5% in the [trans-RuCl$_4$(DMSO) (NH$_3$)] NH$_4$.

Example (ii)-C
Materials and methods

Two groups of 7 and one group of 9 (controls) of female CBA mice of 22 g obtained from a colony grown according to the procedures for kin animals, were inoculated by intramuscular injection with $10^6$ cells of MCa mammary carcinoma as reported in the test (ii)-A.

From the 9th to the 14th day, the three groups of mice were daily treated intraperitoneally as follows:

Group 1—Control: 10 ml/kg of body weight/day of a sterile and pyrogen-free physiological solution;

Group 2—10 mi/kg of body weight/day of a sterile and pyrogen-free physiological solution containing 44 mg of [trans-RuCl$_4$(DMSO)(NH$_3$)]Na 2DMSO, as described in the above mentioned WO 90/13553 international patent application;

Group 3—10 ml/kg of body weight /day of a sterile and pyrogen-free physiological solution containing 27 mg of [trans-RuCl$_4$(DMSO) (NH$_3$)]NH$_4$ (Example 5).

In order to evaluate the activity of the salts of the invention on the primary tumor, the average weight of the primary tumor at the beginning and in the end of the treatment with the salts of the invention, as well as the percentage variation of the growth were assessed.

The obtained results are reported herebelow in Table 11, showing the weight of the primary tumor at the beginning and at the end of the treatment, as well as the growth % variation.

Table 11: effect exerted by the compounds according to the present invention on the growth of the primary tumor of the mice affected by MCa mammary carcinoma.

| | mg weight of the primary tumor | | |
|---|---|---|---|
| compound | beginning of treatment | end of treatment | (%) growth |
| Control | 355 ± 31 | 813 ± 109 | +229 |
| [trans-RuCl$_4$(DMSO) (NH$_3$)]Na 2DMSO | 367 ± 46 | 681 ± 62 | +186 |
| [trans-RuCl$_4$(DMSO) (NH$_3$)] NH$_4$ | 410 ± 17 | 633 ± 38* | +154 |

*p < 0,05 with respect to the control group; t-test for grouped data.

From the figures reported above, it is evident that the reduced growth of the primary tumor in the groups treated with the salts of Ru(III) complexes, as normalized by the controls, is 18.7% for [trans-RuCl$_4$(DMSO) (NH$_3$)]Na 2DMSO while it is 32.8% in [trans-RuCl$_4$(DMSO) (NH$_3$)]NH$_4$. These figures show that the [trans-RuCl$_4$(DMSO) (NH$_3$)]NH$_4$ of the present invention can exert antitumor effects on the growth of the primary tumor which are remarkably higher with respect to the known compounds in the state-of-the-art.

Example (ii)-D

Materials and Methods

Three groups of 7 female CBA mice of 23±2 g, obtained from a colony grown according to the procedures for kin animals. The colony obtained originally from Chester Beatthy Institute of London, was subsequently kept by means of serial couplings between kins (brother and sister) in a ratio ranging from 1:1 to 1:4. The couplings took place at the peak of the sexual maturity of the animals born in the 5th week. Animals underweight or with evident organic anomalies were discarded.

The three groups were inoculated by intramuscular injection, with $10^6$ MCa mammary carcinoma cells suspended in 0.05 ml of a Dulbecco's buffered calcium and magnesium-free physiological solution (PBS) using a sterile syringe. The tumor line was obtained from Rudjer Boskovic Institute in Zagabria and maintained in liquid nitrogen.

13 days after inoculation, the primary tumor was surgically removed.

From day 14 to 19, the three groups of mice were treated intraperitoneally as follows:

Group 1—Control: 10 ml/kg of body weight/day of a sterile and pyrogen-free physiological solution;

Group 2—10 ml/kg of body weight/day of a sterile and pyrogen-free physiological solution containing 2 mg of Cisplatin Group 3—10 ml/kg of body weight/day of a sterile and pyrogen-free physiological solution containing 35 mg of [trans-RuCl$_4$(DMSO) (Im)][ImH] (Example 2).

Table 12: Comparison of antimetastatic effect of [trans-RuCl$_4$(DMSO) (Im)][ImH] of Example 2 (35 mg/kg/day) with respect to Cisplatin (2 mg/kg/day) on mice affected by MCa mammary carcinoma.

| compound | Effect on lung metastases Days of survival (mean ± SE) |
|---|---|
| control | 17,4 ± 1,2 |
| [trans-RuCl$_4$(DMSO) (Im)][ImH] | 24,4 ± 2,2* |
| Cisplatin | 24,3 ± 1,7* |

*p < 0.05 vs controls

Example (ii)-E

In vivo Activity Test of the Salts (I), according to the Present Invention, on Mice Affected by TS/A Mammary Adenocarcinoma.

Materials and methods

Three groups, each made up of 10 female BALBc mice of 21±1 g, obtained from Harlan Nossan (Italia) were inoculated by intramuscular injection, with $10^5$ TS/a mammary adenocarcinoma cells suspended in 0.05 ml of a Dulbecco's buffered calcium and magnesium-free solution (PBS) using a sterile insulin syringe.

The tumor line was obtained from Istituto immunogenetica (Univ. Torino, IT) and maintained in liquid nitrogen.

From the 13th to the 18th day, the three groups of mice were treated intraperitoneally as follows:

Group 1—Control: 10 ml/kg of body weight/day of a sterile and pyrogen-free physiological solution;

Group 2—10 ml/kg of body weight/day of a sterile and pyrogen-free physiological solution containing 2 mg of Cisplatin Group 3—10 ml/kg of body weight/day of a sterile and pyrogen-free physiological solution containing 35 mg of [trans-RuCl$_4$(DMSO) (Im)][ImH] (Example 2).

19 days after inoculation, the primary tumor was surgically removed.

33 days after inoculation, the mice were sacrificed by cervical dislocation and the lung metastases were counted. The lungs were abducted immediately after death of the mice and were divided in single lobes, which were then subsequently examined by the use of a low magnification stereoscopic microscope, equipped with a grid on the eyepiece, which allowed the detection of a and b orthogonal axes (where a≦b).

The lung metastases were then classified according to their dimensions and the weight of the metastases for each animal was then calculated as the sum of the weight of each single metastases, each one regarded as a solid by means of the formula $(\pi/6) a^2 \times b$. The experimental data obtained were then processed with the Student-Newmann-Keuls statistical test.

The results obtained are hereunder reported in Table 13, where the number of metastases and their weight in both groups of treated mice (2) and (3) are reported with respect to the control Group (1). The figures are reported as the average ±S. E. of the single values obtained for each group.

Table 13: Antimetastatic activity on mice affected by TS/A mammary adenocarcinoma, of [trans-RuCl$_4$(DMSO)(Im)][ImH] of Example 2 (35 mg/kg/day) with respect to Cisplatin (2 mg/kg/day).

| compound | N° of lung metastases | weight of lung metastases (mg) |
| --- | --- | --- |
| control | 7,3 ± 3,0 | 10,4 ± 3.1 |
| [trans-RuCl$_4$(DMSO) (Im)][ImH] | 1,7 ± 0,5* | 0,4 ± 0,1* |
| Cisplatin | 3,70 ± 1,0* | 1,6 ± 0,6* |

*P < 0.05 vs controls; test-t for grouped data.

The dosages chosen for the comparison of the effects of [trans-RuCl$_4$(DMSO) (Im)][ImH] and cisplatin on solid metastasizing tumors are comparable in that they represent the maximum tolerated doses with the treatment adopted (1 injection/day/for 6 consecutive days).

The comparison of the effects of the compound of the invention and cisplatin on the loss of body weight gain during treatment shows that the ruthenium compound (% loss body weight gain vs control=+1(lewis lung car), −6 (Mca mammary car.)) is always less toxic than cisplatin (% loss body weight gain vs control=−11). The comparison of spleen weight of the treated animals (% loss spleen weight vs control=−11) also shows that the drug treatment with the compound of the invention is much better tolerated than that of with cisplatin animals (% loss spleen weight vs control=−52).

On tumor metastasis, the compound of the invention is as effective (Mca mammary carcinoma) or even more effective (Lewis lung carcinoma and TS/A Adenocarcinoma) than cisplatin: It reduces the number of lung metastasis either when given at early stages of tumor growth, ie prior to surgical ablation (TS/A adenocarcinoma) or when it is given to mice with lung metastases in advanced stage of growth, ie after surgical ablation of primary tumour (Lewis lung carcinoma) and the reduction of lung metastases is in agreement with a significant prolongation of the post-surgical life time expentancy of the treated mice (Mca mammary carcinoma)

The in vivo experimental models reported above are related to the treatment, with the compounds of the present invention, of two solid spawning tumors in rodents at an advanced stage of growth. A statistically significant and marked reduction both in the growth of the primary tumor and in the formation of lung metastases is observed. This reduction, as can be seen both in the model (i) of Lewis lung carcinoma and in model (ii) of MCa mammary carcinoma, is to be ascribed to a pronounced inhibition of the growth of lung metastases. In fact, with respect to the controls, the presence of medium/large dimensions in groups of animals treated is notably lower or even inexistent in as far as large nodules are concerned., In particular, from the overall comparison of the data regarding effective reduction in the metastases, the compounds of the present invention are surprisingly more active than the reference compounds known in the state-of-the-art, both in the treatment of the Lewis lung carcinoma and, in a more evident and statistically significant manner, in the treatment of the MCa mammary carcinoma.

What is claimed is:

1. A salt of an anionic complex of Ru(III) with an ammonium cation of formula (I):

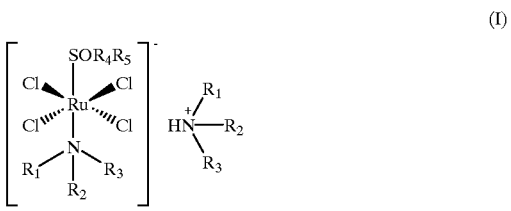

where $R_1$, $R_2$ and $R_3$, equal or different from each other, are selected from the group consisting of H, $C_{1-6}$ alkyl, linear or branched, saturated or unsaturated, $C_3$–$C_7$cycloalkyl, phenyl and aryl;

or $NR_1R_2R_3$ is a 5–7 membered nitrogen-containing heterocycle, saturated or unsaturated, optionally containing one or more O, S and /or N atoms, said nitrogen atom being optionally substituted with a $C_1$–$C_4$ alkyl, aryl or benzyl residue; said nitrogen-containing heterocycle being optionally condensed with a benzo group and/or substituted with $C_1$–$C_4$ alkyl, $C_1$–$C_4$ alkoxyl, $C_1$–$C_4$ alkylthio, aryl or benzyl groups;

where $R_4$ and $R_5$, equal or different from each other, are selected from the group consisting of H, $C_1$–$C_6$ alkyl, $C_3$–$C_7$ cycloalkyl, phenyl and aryl or $R_4$ and $R_5$ form, together with the S atom, a 4–7 membered heterocycle.

2. The salt, according to claim 1, characterized by the fact that $R_1$, $R_2$ and $R_3$, are H or ethyl.

3. The salt, according to claim 1, characterized by the fact that $NR_1R_2R_3$ is a 5-membered nitrogen containing heterocycle selected from the group consisting of imidazole, N-methyl-imidazole, pyrazole, and oxazole.

4. The salt, according to claim 1, characterized by the fact that $NR_1R_2R_3$ is a 6-membered heterocycle selected from the group consisting of pyridine, pyrazine, 3,5 lutidine and 4-methylpyridine.

5. The salt, according to claim 1, characterized by the fact that $NR_1R_2R_3$ is a nitrogen-containing heterocycle being condensed with a benzo group selected from indazole, isoquinoline, benzimidazole and 1,5,6-trimethyl-benzimidazole.

6. The salt, according to claim 1, characterized by the fact that $R_4$—SO—$R_5$ is selected from the group consisting of dimethylsulphoxide, diethylsulphoxide, tetramethylensulphoxide.

7. The salt, according to claim 1, characterized by the fact that $NR_1R_2R_3$ is imidazole and $R_4$—SO—$R_5$ is dimethylsulphoxide.

8. The salt according to claim 1, characterized by the fact that $NR_1R_2R_3$ is $NH_3$ and $R_4$—SO—$R_5$ is dimethylsulphoxide.

9. Process for the preparation of a salt of formula (I), as described in claim 1, comprising the following reaction steps;

1) $RuCl_3$ is reacted with $R_4$—SO—$R_5$ in the presence of HCl to obtain the complex of formula (II)

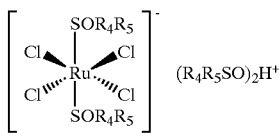 (II)

where $R_4$ and $R_5$ have the meanings reported above;
2) The complex (II), obtained from step (1), is reacted at room temperature with a nitrogen containing compound, $NR_1R_2R_3$, in one or more organic solvents, to obtain the salt of formula (I).

10. The process, according to claim 9, characterized by the fact that $R_4$ and $R_5$ are methyl or ethyl.

11. The process, according to claim 9, characterized by the fact that, in step (1), $RuCl_3$ is dissolved in an organic solvent and the solution obtained in this way is reacted with $R_4$—SO—$R_5$ and concentrated HCl, at a temperature ranging from 60 to 90° C.

12. The process, according to claim 11, characterized by the fact that $RuCl_3$ dissolved in ethanol or methanol and the solution obtained in this way is reacted with $R_4$—SO—$R_5$ and concentrated HCl, at a temperature of about 80° C.

13. The process, according to claim 9, characterized by the fact that, in step (2), said complex (II) and said nitrogen-containing compound, $NR_1R_2R_3$, are reacted in molar ratios ranging from 1:2 to 1:6.

14. The process, according to claim 9, characterized by the fact that, in step (2), said organic solvents are acetone or dichloromethane.

15. A therapeutic method of treating metastases and neoplasias, characterized by administering at least one salt of formula (I), as described in claim 1.

16. The method, according to claim 15, in the treatment of solid tumors which produce metastases.

17. The method, according to claim 16, characterized by the fact that said solid tumors are selected from the group consisting of carcinomas of the gastrointestinal tract, mammary carcinomas, lung tumors, metastatic carcinomas, and lung metastases of metastatic tumors.

18. The method, according to claim 15, characterized by the fact that said salts of formula (I) are administered in amounts ranging from 0.1 to 300 mg/kg/day, in single or multiple doses.

19. The method, according to claim 15, characterized by the fact that said salts of formula (I) are administered by parenteral, oral, topical or transdermal routes.

20. A pharmaceutical composition containing, as an active compound, a therapeutically effective amount of at least one of the salts of formula (I), as defined in claim 1, in combination with suitable excipients and diluents.

21. The pharmaceutical composition according to claim 20, characterized by the fact that it is in the form of solution or suspension.

22. The pharmaceutical composition according to claim 20, characterized by the fact that it is in the form of gel, ointment, powder, pill, tablet, capsule or insert.

23. The pharmaceutical composition, according to claim 20, characterized by the fact that said salts of formula (I) are combined with one or more antitumor drugs.

* * * * *